(12) United States Patent
Kimoto

(10) Patent No.: US 8,036,620 B2
(45) Date of Patent: Oct. 11, 2011

(54) RECEIVING APPARATUS

(75) Inventor: Seiichiro Kimoto, Tokyo (JP)

(73) Assignee: Olympus Corporation (JP)

( * ) Notice: Subject to any disclaimer, the term of this patent is extended or adjusted under 35 U.S.C. 154(b) by 980 days.

(21) Appl. No.: 11/573,850

(22) PCT Filed: Sep. 21, 2006

(86) PCT No.: PCT/JP2006/318771
§ 371 (c)(1),
(2), (4) Date: Feb. 16, 2007

(87) PCT Pub. No.: WO2007/034890
PCT Pub. Date: Mar. 29, 2007

(65) Prior Publication Data
US 2008/0318541 A1    Dec. 25, 2008

(30) Foreign Application Priority Data

Sep. 22, 2005   (JP) .................................. 2005-275667

(51) Int. Cl.
*H04B 1/06* (2006.01)
*H04B 7/00* (2006.01)
*H04M 1/00* (2006.01)

(52) U.S. Cl. .................. 455/272; 455/277.1; 455/277.2; 455/562.1; 455/575.7

(58) Field of Classification Search .................. 455/272, 455/277.1, 277.2, 562.1, 575.7
See application file for complete search history.

(56) References Cited

U.S. PATENT DOCUMENTS 6,801,782 B2 * 10/2004 McCrady et al. ............. 455/517
7,251,503 B2 * 7/2007 Shirakata et al. .......... 455/562.1
2001/0001760 A1   5/2001 Taira
2005/0148306 A1 * 7/2005 Hiddink .......................... 455/101
2009/0312604 A1 * 12/2009 Kimoto et al. ................. 600/118

FOREIGN PATENT DOCUMENTS

EP        1 679 029 A1    7/2006
EP        1702554         9/2006
JP        2003-19111      1/2003

(Continued)

OTHER PUBLICATIONS

PCT Form 304 and Notification Concerning Availability of Publication issued in connection with corresponding PCT Appln. No. PCT/JP2006/318771 dated Dec. 22, 2006.
PCT International Search Report issued Dec. 12, 2006 in corresponding PCT Application No. PCT/JP2006/318771.
PCT International Written Opinion issued Dec. 12, 2006 in corresponding PCT Application No. PCT/JP2006/318771.

(Continued)

*Primary Examiner* — Wen Huang
(74) *Attorney, Agent, or Firm* — Ostrolenk Faber LLP

(57) ABSTRACT

In order to restore synchronization quickly in the case where synchronization with a transmission signal is not established, when a synchronization signal is not received by an antenna selected in advance in a receiving apparatus (2), a selection controller (C2) continuously switches between antennas (6a to 6h), repeats an antenna switching process for measuring received strengths of the respective antennas in a cycle shorter than a transmission period of transmission information in a radio signal so as to detect an antenna with maximum strength, selects and switches to the detected antenna with maximum strength as a receiving antenna for receiving synchronization information, and continues the connection until at least the synchronization information is received. Further, the selection controller (C2) makes a control so that the antenna switching process for detecting the antenna with maximum strength is repeated for a period longer than a non-transmission period of transmission information.

14 Claims, 16 Drawing Sheets

FOREIGN PATENT DOCUMENTS

| | | |
|---|---|---|
| JP | 2005-252727 | 9/2005 |
| JP | 2005-253797 | 9/2005 |
| WO | WO 2005/065525 | 7/2005 |
| WO | WO 2005/084521 | 9/2005 |

OTHER PUBLICATIONS

Search Report issued by European Patent Office in connection with corresponding application No. EP 06 79 8210 on Dec. 29, 2010.

* cited by examiner

FIG.12

| ANTENNA SCANNING PERIOD | RECEIVED STRENGTH | | | | | | | |
|---|---|---|---|---|---|---|---|---|
| | No.1 | No.2 | No.3 | No.4 | No.5 | No.6 | No.7 | No.8 |
| AS1 | 80 | 11 | 10 | 9 | 11 | 10 | 9 | 11 |
| AS2 | 80 | 11 | 10 | 9 | 7 | 8 | 6 | 5 |
| AS3 | 7 | 8 | 7 | 6 | 8 | 7 | 6 | 8 |

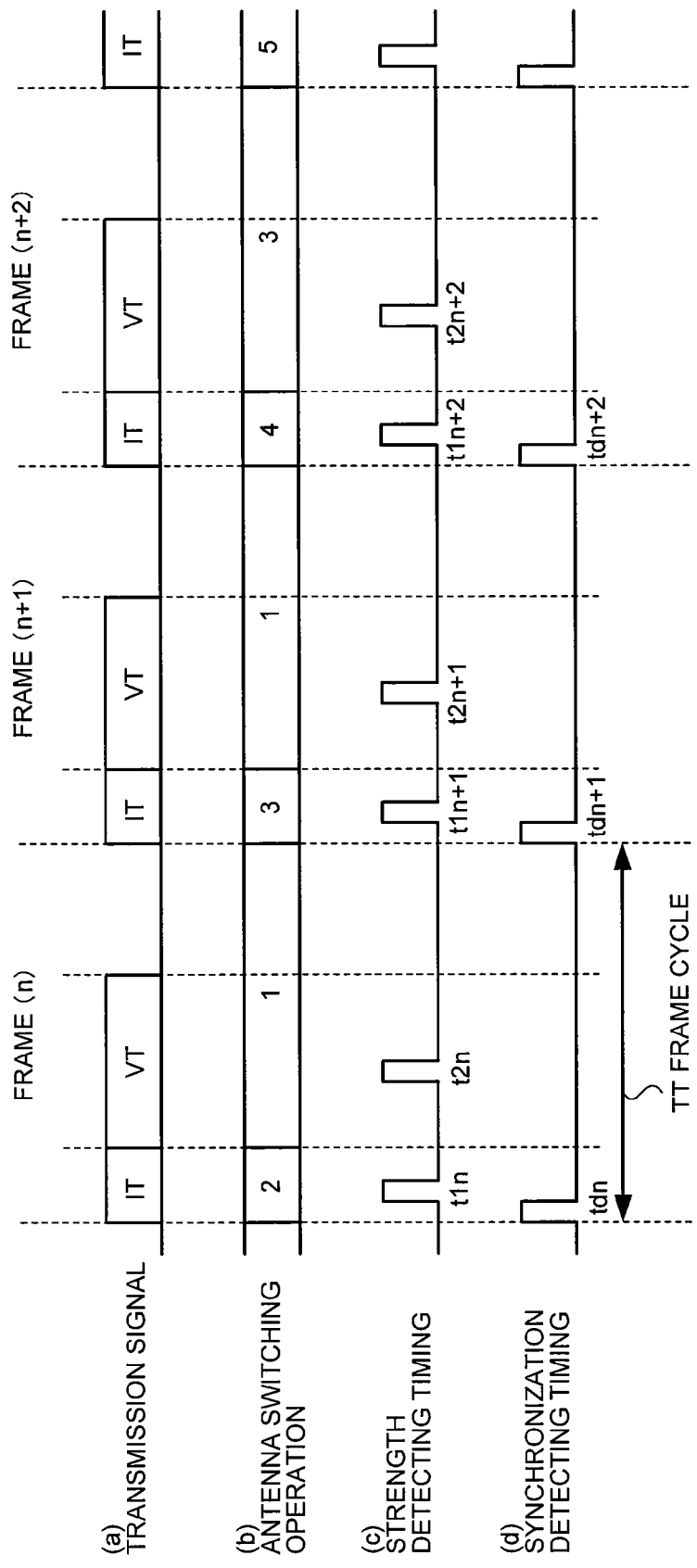

RECEIVING APPARATUS

CROSS REFERENCE TO RELATED APPLICATION

The present application is a 35 U.S.C. §§371 national phase conversion of PCT/JP2006/318771, filed 21 Sep. 2006, which claims priority of Japanese Patent Application No. 2005-275667 filed 22 Sep. 2005, which is herein, incorporated by reference.

TECHNICAL FIELD

The present invention relates to a receiving apparatus which has at least an information main body section including information main body and an adding section including information for measurement of received electric field strength, and selectively receives a radio signal of a frame construction including synchronization information in at least one of the information main body section and the adding section by using a plurality of antennas, and particularly relates to a receiving apparatus which receives a radio image signal transmitted from a capsule endoscope in a subject by using a plurality of antennas outside the subject.

BACKGROUND ART

In recent years, swallowable capsule endoscopes are being developed in the field of endoscopes. The capsule endoscopes have an image pickup function and a radio communication function. While the capsule endoscope is swallowed through a subject's mouth and is ejected naturally in order to observe the insides of various internal organs, it moves along the insides of internal organs such as belly, small intestine and large intestine according to their peristaltic activities and simultaneously picks up images sequentially.

Image data, which are picked up by the capsule endoscope in the subject while the capsule endoscope is moving inside the organs, are sequentially transmitted to the outside of the subject by using radio signals and are stored in a memory provided into a receiver outside of the subject or are displayed on a display provided to the receiver. Doctors, nurses and the like can carry out diagnosis based on the images which are displayed on the display according to the image data stored in the memory or the images which are displayed on the display provided to the receiver at the same time of reception.

Generally as to the receiver, in the case where the image data are stored in the memory, a plurality of antennas for receiving image signals transmitted from the capsule endoscope are dispersively arranged outside the subject, and one antenna which receives image signals with less errors is selected so as to receive the images. For example, Patent Document 1 discloses a receiver which switches reception between plural antennas arranged outside a subject, and tracks a position of a capsule endoscope in the subject as a transmission source of image signals based on electric field strength received by the antennas.

Patent Document 1: Japanese Patent Application Laid-Open No. 2003-19111

DISCLOSURE OF INVENTION

Problem to be Solved by the Invention

However, in conventional receivers, for example, just after reception of an image signal is started, the image signals transmission period on a capsule endoscope side or the period for transmission of signals for measuring received electric field strength of preamble or the like is occasionally not synchronized with detection timing of received electric field strength on the receiver side, and thus the received electric field strength cannot be measured or is measured improperly.

The present invention is devised in view of the above problem and its object is to provide a receiving apparatus which can restore synchronization quickly when synchronization with a transmitted radio signal is not established, can receive an image signal or the like and measure received electric field strength securely, and can further improve reliability of a receiving operation.

Means for Solving Problem

A receiving apparatus according to one aspect of the present invention selectively receives a radio signal through a plurality of antennas, the radio signal having transmission information including at least synchronization information transmitted in a predetermined transmission cycle. The receiving apparatus also includes a control unit which, when the synchronization information is not received through an antenna selected in advance, repeats an antenna switching process that continuously switches between the plurality of antennas to measure received electric field strengths of the respective antennas in a cycle shorter than a transmission period of the transmission information, and makes a control for detecting an antenna with maximum strength whose received electric field strength is the largest, and selecting and switching to the antenna with maximum strength as a receiving antenna for receiving the synchronization information.

A receiving apparatus according to another aspect of the present invention selectively receives a radio signal through a plurality of antennas, the radio signal having transmission information including at least synchronization information transmitted in a predetermined transmission cycle. The receiving apparatus also includes a control unit which, when the synchronization information is not received through an antenna selected in advance, repeats an antenna switching process that continuously switches between the plurality of antennas to measure received electric field strengths of the respective antennas for a period longer than a non-transmission period obtained by subtracting a transmission period from the transmission cycle, and makes a control for detecting an antenna with maximum strength whose received electric field strength is the largest, and selecting and switching to the antenna with maximum strength as a receiving antenna for receiving the synchronization information.

In the receiving apparatus, the control unit may make a control for continuously repeating the antenna switching process.

In the receiving apparatus, the control unit may give a series of antenna numbers to the plurality of antennas, respectively and switches between the antennas in an antenna numerical order to execute the antenna switching process.

In the receiving apparatus, after the control unit selects and switches to the antenna with maximum strength as the receiving antenna for receiving the synchronization information, the control may make a control for continuing a connection until at least the synchronization information is received.

Further, in the receiving apparatus, the transmission information may include an information main body section including an information main body and an adding section including the synchronization information. When the synchronization information is received through the antenna selected in advance, the control unit may sequentially switch between the plurality of antennas for a transmission period of the adding section to measure received electric field strengths of the antennas, and select and switch to an antenna having the largest received electric field strength as a receiving antenna for receiving the information main body section.

Further, in the receiving apparatus, the radio signal may be a signal having a frame constitution having an information main body section including an information main body and an adding section including the synchronization information. When the synchronization information of a current frame is received through the antenna selected in advance, the control unit may measure a received electric field strength of a first antenna within a transmission period of the adding section of the current frame, measure a received electric field strength of a second antenna within a transmission period of the information main body section of the current frame, and when the received electric field strength of the first antenna exceeds the received electric field strength of the second antenna, the control unit select and switch to the first antenna as a receiving antenna for receiving the information main body section of a next frame.

In the receiving apparatus, the radio signal may be a signal which is transmitted from a transmission apparatus, the transmission apparatus being introduced into a subject and moving in the subject, and the information main body includes in-vivo image information obtained by imaging an inside of the subject.

EFFECT OF THE INVENTION

According to the receiving apparatus of the present invention, when synchronization with the transmitted radio signal is not established, the synchronization can be restored, the image signal or the like can be received and the received electric field strengths can be measured securely, and reliability of the receiving operation can be further improved.

BRIEF DESCRIPTION OF DRAWINGS

FIG. 12 is a diagram illustrating a concrete example of a received strength detected result by means of the synchronization restoring antenna switching process;

FIG. 16 is a time chart illustrating the antenna switching process in the case where a synchronization signal is received.

EXPLANATIONS OF LETTERS OR NUMERALS

Figure 1:
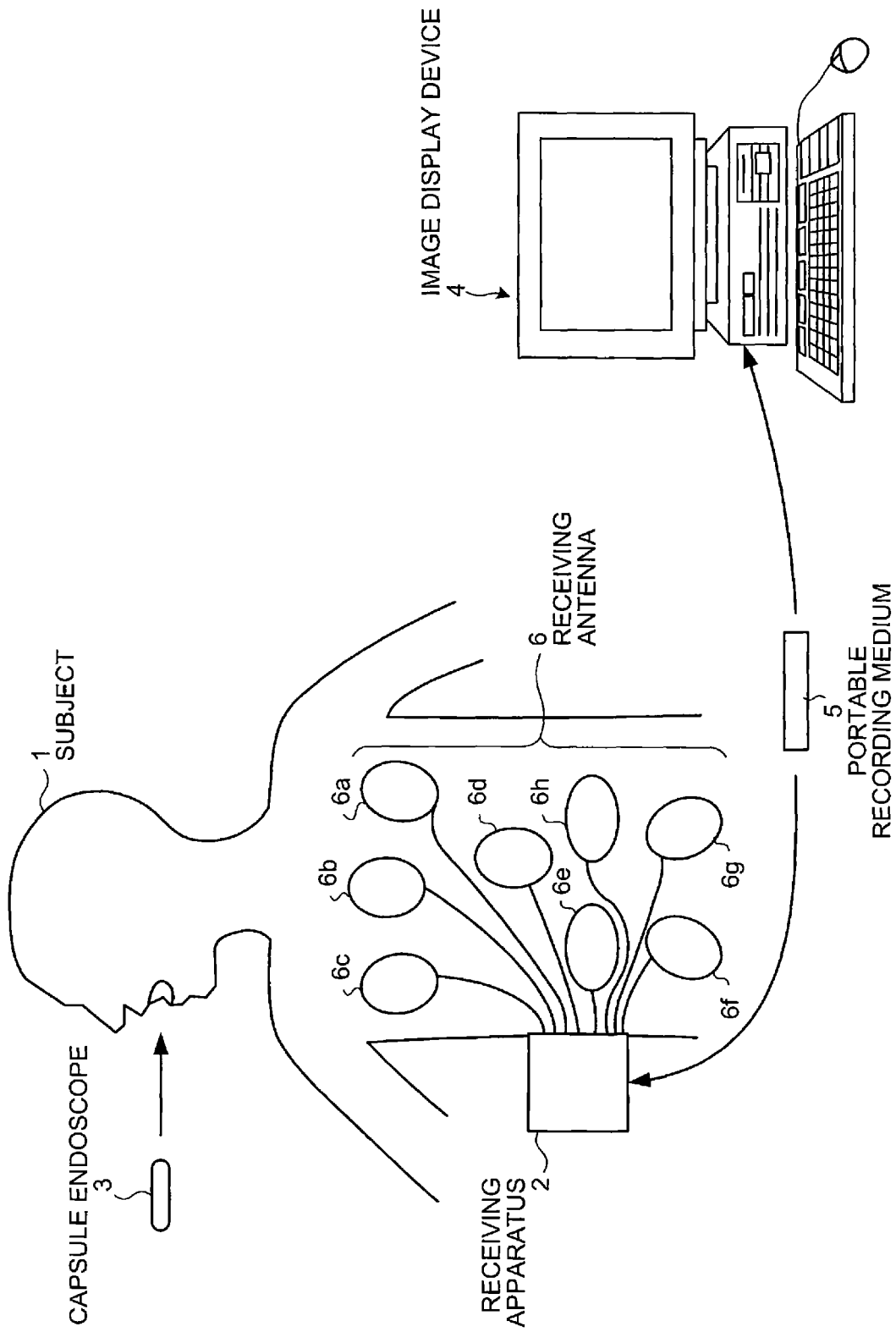
FIG. 1 is a schematic diagram illustrating an entire constitution of a wireless in-vivo information acquiring system including a receiving apparatus according to an embodiment of the present invention.

1 Subject
2 Receiving apparatus
3 Capsule endoscope
4 Display device
5 Portable recording medium
6 Receiving antenna
6a to 6h Antenna
11 Receiving circuit
12 Signal processing circuit
13 Storage unit
14 Display unit
15 Synchronization detector
16 A/D converter
17 Power supply unit
C1 Control unit
C2 Selection controller
C2a Strength storage unit
C2b Strength comparator
C2c Switching controller
SC Switching controller
SW Changeover switch
S1 Demodulated signal
S2 Received strength signal

BEST MODE(S) FOR CARRYING OUT THE INVENTION

A wireless in-vivo information acquiring system which is a preferable embodiment of a receiving apparatus of the present invention will be explained in detail below with reference to the accompanying drawings. The present invention is not limited to the embodiment. Further, in the description of the drawings, like members are designated by like reference numbers.

EMBODIMENT

First, the wireless in-vivo information acquiring system having a receiving apparatus according to an embodiment will be explained. FIG. 1 is a schematic diagram illustrating an entire constitution of the wireless in-vivo information acquiring system. The wireless in-vivo information acquiring system uses a capsule endoscope as one example of a device to be introduced into a subject.

As shown in FIG. 1, the wireless in-vivo information acquiring system is provided with a capsule endoscope 3 which is introduced into a subject 1 and radio-transmits image data of picked-up images of the inside of the subject to a receiving apparatus 2, the receiving apparatus 2 which receives the image data radio-transmitted from the capsule endoscope 3, an image display device 4 which displays the images of the inside of the subject based on an image signal received by the receiving apparatus 2, and a portable recording medium 5 which sends and receives the image data or the like between the receiving apparatus 2 and the image display device 4.

The receiving apparatus 2 is provided with a receiving antenna 6 having a plurality of antennas 6a to 6h which are pasted to a body surface of the subject 1. The receiving apparatus 2 receives the image data or the like radio-transmitted from the capsule endoscope 3 via the receiving antenna 6. The antennas 6a to 6h are realized by using, for example, loop antennas, and are arranged in predetermined positions on the body surface of the subject 1, namely, positions corresponding to organs in the subject 1 as a passing route of the capsule endoscope 3.

The antennas 6a to 6h may be disposed in predetermined positions of a jacket or the like on the subject 1. In this case, the antennas 6a to 6h are disposed in predetermined positions on the body surface of the subject 1 via the jacket or the like. Further, the arrangement of the antennas 6a to 6h can be arbitrarily changed according to objects such as observation and a diagnosis of the subject 1. The number of antennas of the receiving antenna 6 is not necessarily limited to eight, namely, antennas 6a to 6h, and thus the number may be smaller than eight.

The image display device 4 is realized by a work station having CRT, liquid crystal display or the like, and displays an image based on image data acquired via the portable recording medium 5 or the like. Further, the image display device 4 can output and display the image data on an output device such as a printer. The image display device 4 has a function for communicating with external devices, and may acquire or output the image data by means of wired or wireless communication.

The portable recording medium 5 is realized by a CompactFlash® memory, CD or DVD, and it is detachable from the receiving apparatus 2 and the image display device 4, and when it is attached to them, various information such as image data can be output or recorded from/into the portable recording medium 5. The portable recording medium 5 is attached to the receiving apparatus 2 while, for example, the capsule endoscope 3 is introduced into the subject 1, and the receiving apparatus 2 records the image data or the like received from the capsule endoscope 3. Further, after the capsule endoscope 3 is discharged from the subject 1, the portable recording medium 5 is taken out from the receiving apparatus 2 and is attached to the image display device 4, so that the recorded image data or the like are output to the image display device 4.

The image data are sent and received between the receiving apparatus 2 and the image display device 4 by means of the portable recording medium 5, so that the subject 1 can freely act while the capsule endoscope 3 is in the subject 1. The data may be send and received between the receiving apparatus 2 and the image display device 4 by means of wired or wireless communication.

Figure 2:
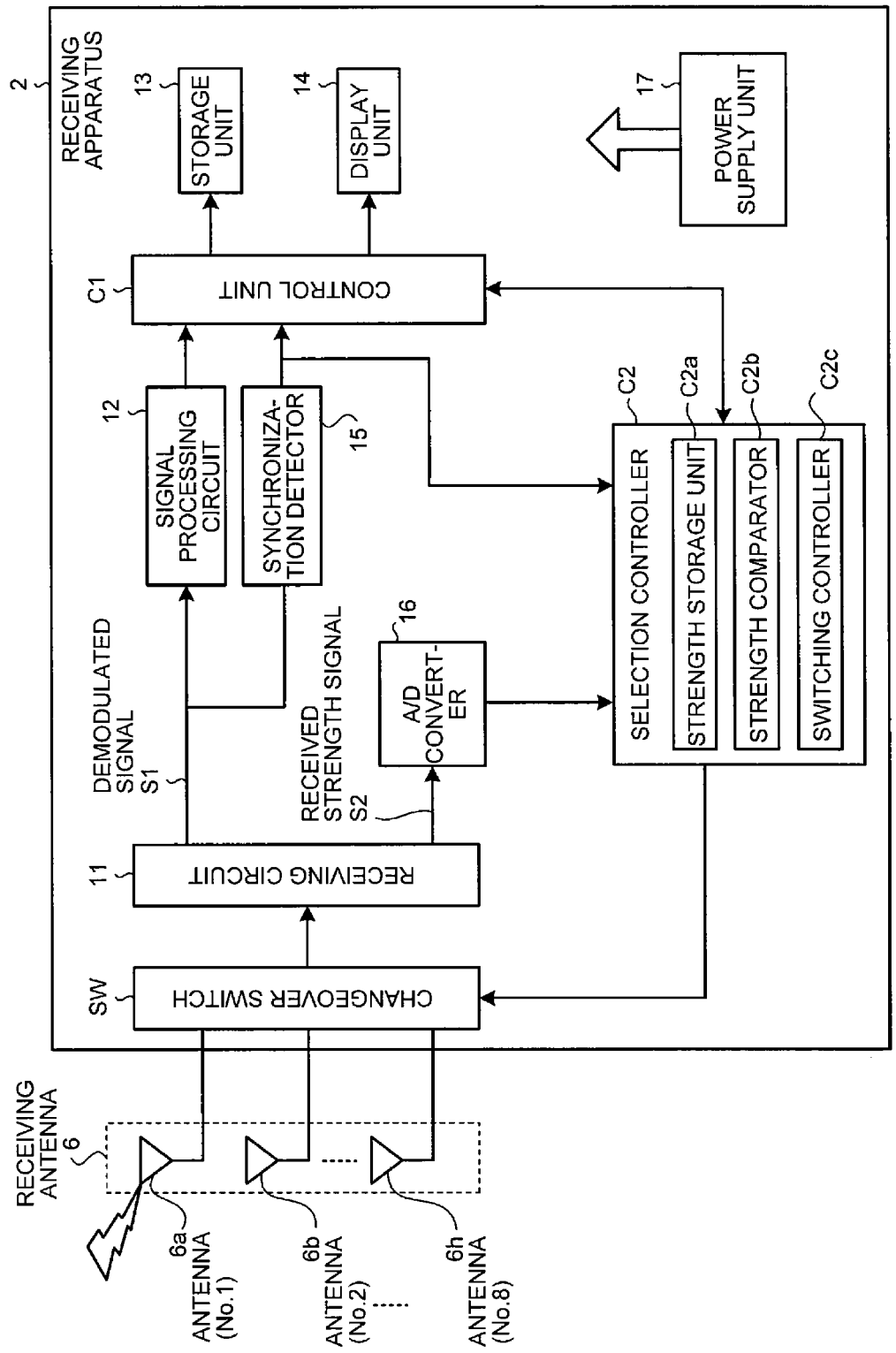
FIG. 2 is a block diagram illustrating a constitution of the receiving apparatus shown in FIG. 1.

The receiving apparatus 2 will be explained with reference to FIG. 2. FIG. 2 is a block diagram illustrating a constitution of the receiving apparatus 2. As shown in FIG. 2, the receiving apparatus 2 has a function for processing a radio signal transmitted from the capsule endoscope 3. Specifically, the receiving apparatus 2 has a changeover switch SW for continuously switching connection of the antennas 6a to 6h with a series of antenna numbers, a receiving circuit 11 which is connected to a later tier of the changeover switch SW and amplifies radio signals from the antennas 6a to 6h switched to be connected by the changeover switch SW so as to demodulate the signals, a signal processing circuit 12 which is connected to a later tier of the receiving circuit 11, a synchronization detector 15 and an A/D converter 16.

A control unit C1 connects a storage unit 13, a display unit 14 and a selection controller C2 corresponding to the signal processing circuit 12, the synchronization detector 15, the A/D converter 16 and the portable recording medium 5. The selection controller C2 has a strength storage unit $C2a$, a strength comparator $C2b$ and a changeover control section $C2c$, and gives a switching instruction to the changeover switch SW and simultaneously instructs processing timing of the synchronization detector 15, the A/D converter 16 and the control unit C1. A power supply unit 17 supplies an electric power to the above-mentioned respective sections, and is realized by, for example, a battery.

The changeover switch SW selectively connects any one of the antennas 6a to 6h based on the switching instruction from the selection controller C2, and outputs radio signals from connected antennas 6a to 6h to the receiving circuit 11. The receiving circuit 11 amplifies the input radio signals, outputs modulated signals S1 to the signal processing circuit 12 and the synchronization detector 15, and outputs received strength signals S2 as the received electric field strengths of the amplified radio signals to the A/D converter 16.

The signal processing circuit 12 outputs the image data processed based on the demodulated signal S1 to the control unit C1, and the control unit C1 stores the image data into the storage unit 13 and display them on the display unit 14. The synchronization detector 15 extracts synchronization information included in the demodulated signals S1, and outputs them to the control unit C1 and the selection controller C2. The control unit C1 and the selection controller C2 execute various processes on the acquired synchronization information, such as s a receiving process for a radio signal according to the process timing. The A/D converter 16 converts the input received strength signals S2 into digital signals so as to output them to the selection controller C2.

The selection controller C2 refers to the synchronization information output from the synchronization detector 15. When the synchronization signal has been received, the selection controller C2 continuously switches between the antennas 6a to 6h within the period for measuring the received strength of a radio signal, mentioned later, so as to measure the received electric field strengths of the respective antennas. The selection controller C2 selects and switches to the antenna having the largest received electric field strength as a receiving antenna for receiving an image signal.

On the other hand, when the synchronization signal is not received, in order to restore the synchronization with the radio signal, the selection controller C2 repeats the antenna switching process for continuously switching between the antennas 6a to 6h and measuring the received electric field strengths of the antennas in a cycle which is shorter than a total period of the received strength measuring period as the transmission period of transmission information of the radio signal and the image signal period, so as to detect the antenna with maximum strength whose received electric field strength is the largest. The selection controller C2 selects and switches to the detected antenna with maximum strength as the receiving antenna for receiving the synchronization information, so as to continue its connection until at least the synchronization signal is received. The selection controller C2 may make a control so that the antenna switching process for detecting the antenna with maximum strength is repeated for a period longer than the non-transmission period obtained by subtracting the transmission period of the transmission information from the transmission cycle of the radio signal.

Figure 3:
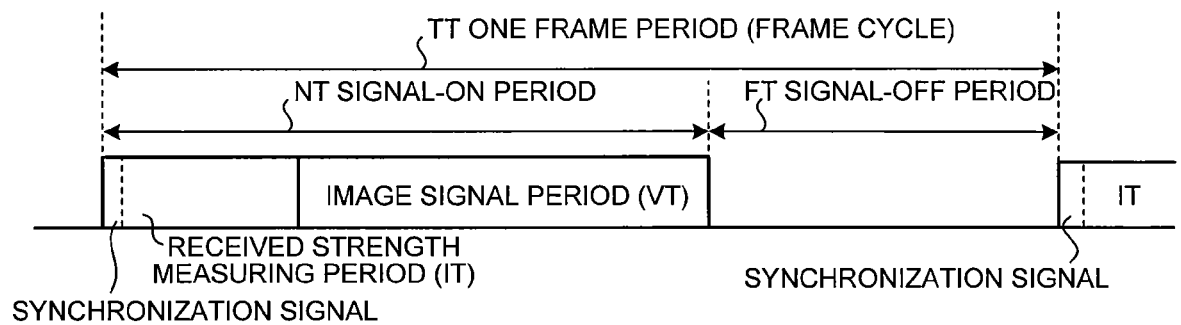
FIG. 3 is a diagram illustrating a frame format of a radio signal transmitted from a capsule endoscope shown in FIG. 1.

More concretely, the summary of the antenna switching process controlled by the selection controller C2 will be explained below with reference to FIGS. 3 to 6. The radio signal from the capsule endoscope 3 will be explained first. As shown in FIG. 3, with the radio signal transmitted from the capsule endoscope 3, the transmission information is transmitted in a frame unit, and the frame is composed of the received strength measuring period (IT) and the image signal period (VT). The received strength measuring period is a period corresponding to a preamble signal period for adjusting reception, and the head of the period includes a synchronization signal representing transmission timing from the capsule endoscope 3. The image signal period includes an image signal and also a control signal necessary for receiving the image signal.

As to each frame, in some cases, a non-signal state is present between frames, or each frame is transmitted sequentially. That is, a signal-off period FT as a non-transmission period obtained by subtracting a signal-on period NT as a transmission period for the transmission information in each frame from a frame cycle TT of frame transmission is set to a predetermined period which is 0 or more according to types of radio signals to be transmitted. Further, the length of the frame cycle TT is flexibly adjusted from a viewpoint of the effective use of the battery in the capsule endoscope 3 in such a manner that the length is set to be short in a notable image pickup region or a region where the movement of the capsule endoscope 3 is fast.

Figure 4:
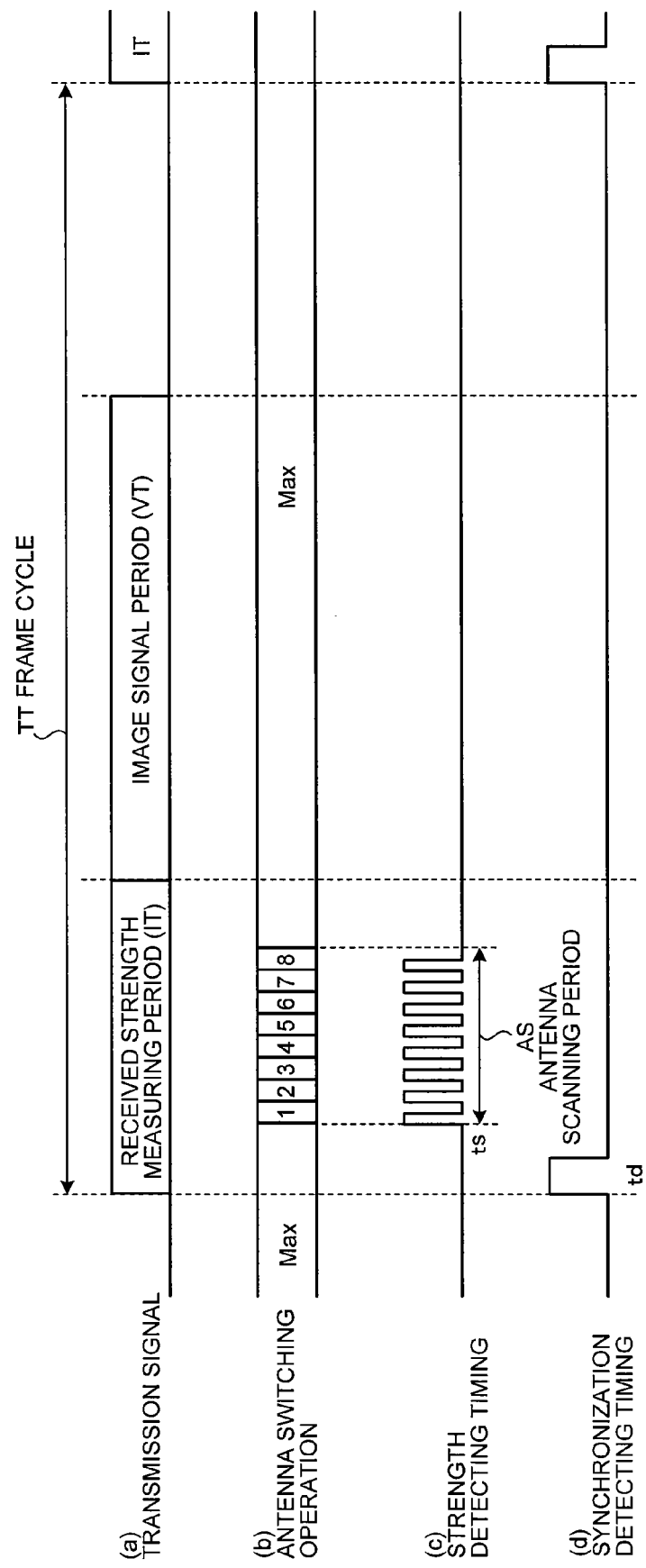
FIG. 4 is a time chart illustrating an antenna switching process in the case where a synchronization signal is received.

The normal antenna switching process executed when the synchronization signal is received will be explained below with reference to a time chart shown in FIG. 4. As shown in FIG. 4, when, at timing td in the received strength measuring period, the synchronization signal is received by an antenna selected in advance and the synchronization information is detected by the synchronization detector 15, the selection controller C2 instructs the changeover switch SW to execute the antenna scanning process as the antenna switching process for sequentially switching between the antennas 6a to 6h at timing ts in the received strength measuring period.

At the antenna scanning process, the selection controller C2 measures the received electric field strength (hereinafter, the received strength) of the antennas 6a to 6h so as to detect the antenna having the largest received strength, and selects the detected antenna as the receiving antenna for the image signal period so as to instruct the changeover switch SW to make the switch to this antenna. For example, the selection controller C2 switches the antenna in order of the antenna numbers 1 to 8 corresponding to the antennas 6a to 6h as shown in FIG. 4 so as to detect the antenna having the largest received strength (Max), and after the antenna scanning process, it makes the switch to the detected antenna (Max). The selection controller C2 executes the antenna scanning process within a predetermined antenna scanning period AS shorter than the received strength measuring period.

In such a manner, the antenna scanning process is executed for each received strength measuring period, and the antenna (Max) having the largest received strength is selected and switched, so that the selection controller C2 can allow the antenna having the largest received strength in each image signal period to receive an image signal.

Figure 5:
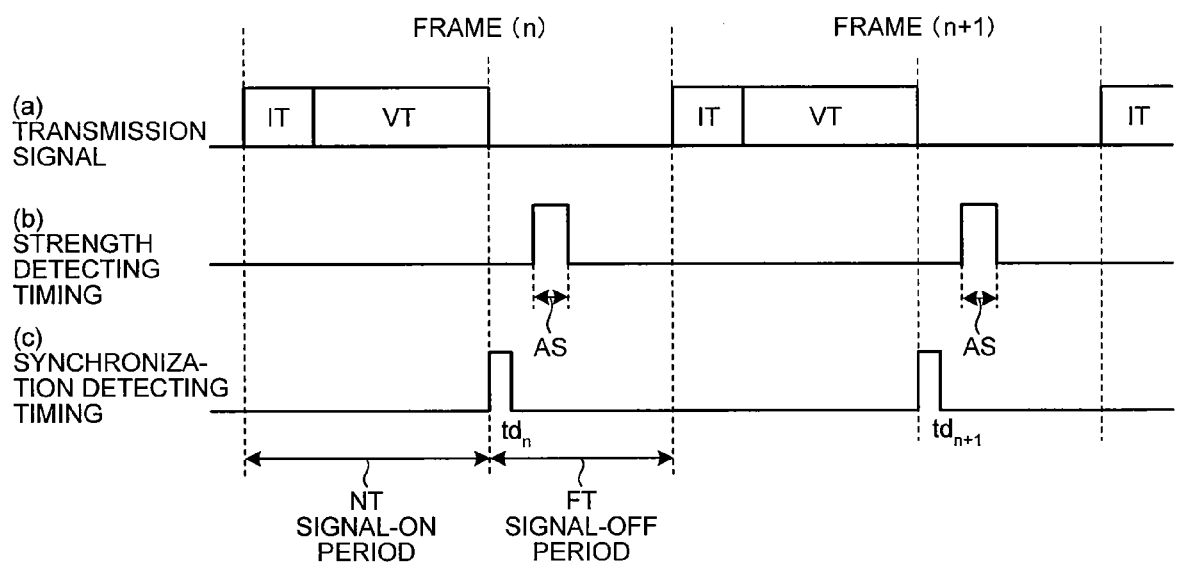
FIG. 5 is a time chart illustrating a signal detecting timing in the case where a synchronization signal is not received.

The antenna switching process for restoring the synchronization which is executed in the case where the synchronization signal is not received will be explained below. As shown in FIG. 5, for example, as to a transmission signal in which the n-th frame (n) and n+1st frame (n+1) are transmitted sequentially, the signal transmitted for the received strength measuring period occasionally cannot be received for the antenna scanning period AS in the above-mentioned normal antenna switching process in the case where respective synchronization detecting timings in the receiving apparatus 2 are $td_n$ and $td_{n+1}$ and are not the timing at which the synchronization signal in each received strength detecting period (IT) can be detected.

Further, in the case of FIG. 5, each antenna scanning period SA is included in the signal-off period FT. For this reason, a received signal cannot be obtained from any antennas switched by the antenna scanning process, and a determination cannot be made which antenna of the antennas 6a to 6h is in a receivable position. At the period where synchronization with the transmission signal is not established (non-synchronous period), each strength detecting timing is determined on the basis of an internal clock of the receiving apparatus 2.

Figure 6:
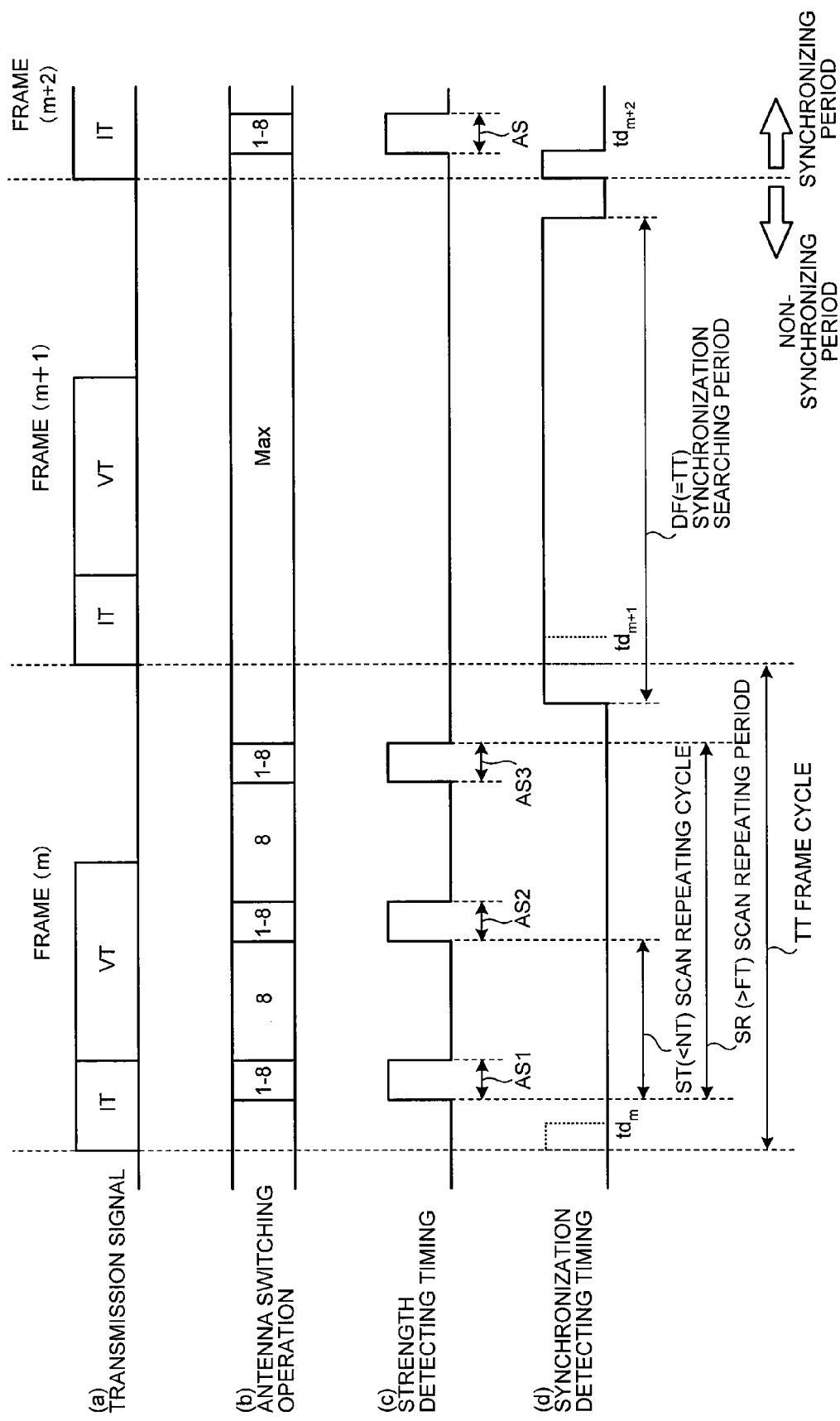
FIG. 6 is a time chart illustrating the antenna switching process in the case where a synchronization signal is not received.

In order to restore the synchronization from the non-synchronous state, the selection controller C2 executes the antenna switching process shown in FIG. 6. That is, in the case where the antenna selected in advance does not receive a synchronization signal, for example, in the case where a synchronization signal of the frame (m) is not received at timing $td_m$ shown in FIG. 6, the selection controller C2 controls the changeover switch SW, so that a scan repeating process for repeating the antenna scanning process in a scan repeating cycle ST shorter than the signal-on period NT. Further, the selection controller C2 makes a control so that the scan repeating process is executed for a scan repeating period SR longer than the signal-off period FT. In the example shown in FIG. 6, the antenna scanning process is repeated three times corresponding to the antenna scanning periods AS1 to AS3 in each scan repeating cycle ST within the scan repeating period SR.

The scan repeating process is executed in such a manner that the selection controller C2 can execute at least one-time antenna scanning process for the signal-on period. According to the antenna scanning process executed for the signal-on period, the respective received strengths of the antennas 6a to 6h can be measured securely, and the antenna in the transmission signal receivable position can be detected, so that the antenna with maximum strength can be detected. In the example of FIG. 6, the antenna scanning periods AS1 and AS2 are included in the signal-on period of the frame (m), the antenna with maximum strength can be detected by the antenna scanning process at the antenna scanning periods AS1 and AS2.

After the antenna with maximum strength is detected by the scan repeating process, the selection controller C2 selects and switches to the detected antenna with maximum strength as the receiving antenna for receiving the synchronization signal, so as to execute a synchronization searching process for searching a synchronization signal. That is, the transmission signal is received continuously by the switched antenna with maximum strength (Max), and the output from the synchronization detector 15 is monitored, so that synchronization information is detected. At this time, the transmission signals are continued to be received for a synchronization searching period DF which is approximately equal to the frame cycle TT, so that the selection controller C2 can detect the synchronization information securely. In the example shown in FIG. 6, the synchronization signal at the frame (m+1) is received at timing $td_{m+1}$, so that the synchronization information can be detected.

When the scan repeating process and the synchronization searching process are executed, the selection controller C2 can restore the synchronization quickly and securely at the time when the synchronization signal is not received. In the example shown in FIG. 6, the synchronization can be restored within the two-frame period including the frames (m) and (m+1) from the time when the synchronization signal is not received, and following frame (m+2), the synchronization signal can be received at timing $td_{m+2}$, so that the sequence is capable of shifting to the normal antenna switching process shown in FIG. 4.

At the above-mentioned scan repeating process, the scan repeating process is continued for the predetermined scan repeating period SR. However, the selection controller C2 ends the scan repeating process at the time when the antenna with maximum strength can be detected, namely, at the time when the respective received strengths of the antennas 6a to 6h can be measured securely, and also the synchronization searching process can be started. Further, at the synchronization searching process, the selection controller C2 can end the synchronization searching process at the time when the synchronization signal can be received and the synchronization information can be detected by the antenna with maximum strength. In other words, after the selection controller C2 connects and switches to the antenna with maximum strength for the synchronization searching process, it may make a control so that the antenna with maximum strength is continued to be connected until at least the synchronization signal is received.

Figure 7:
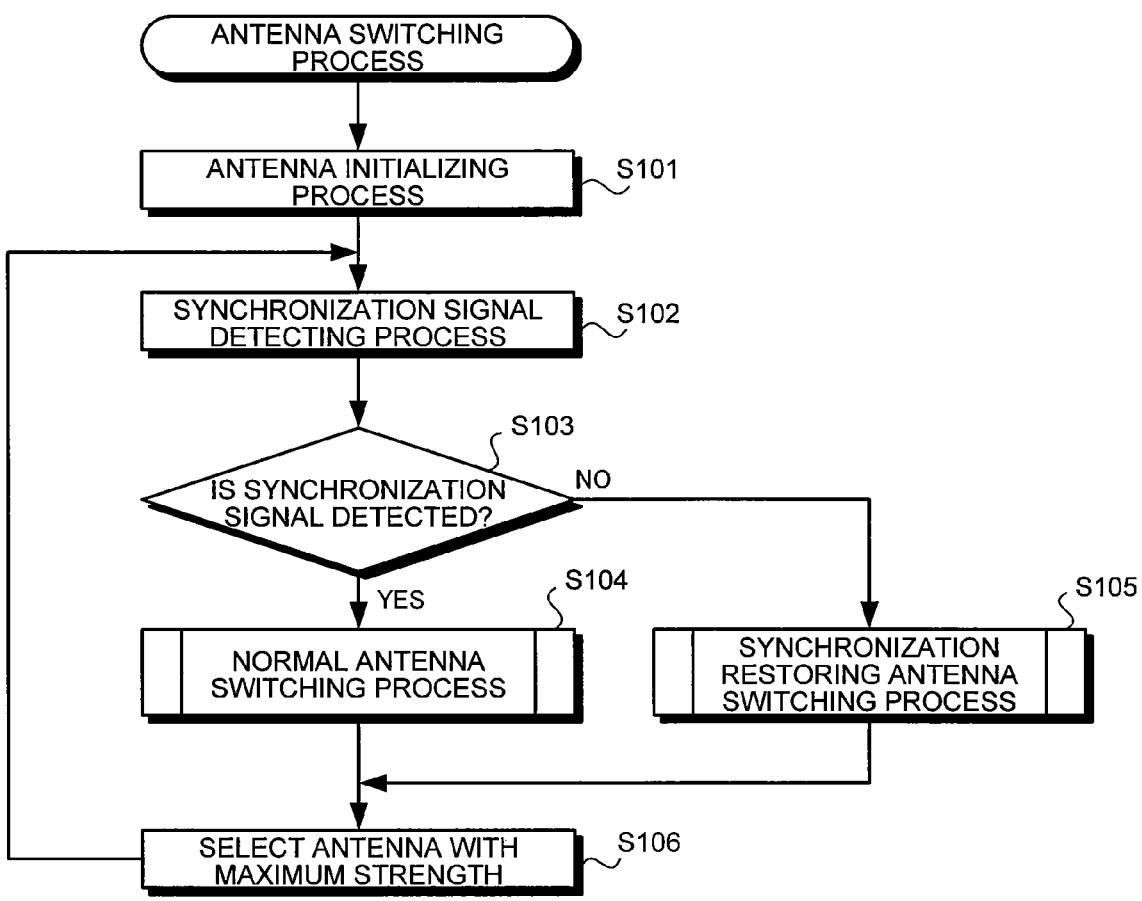
FIG. 7 is a flowchart illustrating the procedure of the antenna switching process by means of the receiving apparatus shown in FIG. 1.

The procedure of the antenna switching process executed by the receiving apparatus 2 will be explained below with reference to a flowchart shown in FIG. 7. The antenna switching process is controlled to be executed by the selection controller C2. As shown in FIG. 7, the selection controller C2 executes an antenna initializing process for selecting an antenna for first reception so as to connect and switches to it as initial setting (step S101). The selection controller C2 selects to switch to and connect, for example, an antenna number 1 as the receiving antenna at step S101. The antenna numbers 1 to 8 which can be set correspond to the antennas 6a to 6h, respectively, as shown in FIG. 2.

Subsequently, the selection controller C2 executes the synchronization signal detecting process for detecting a synchronization signal from a transmission signal at the head of the frame (step S102), and determines whether or not the synchronization signal is detected (step S103). When the synchronization signal is detected (Yes at step S103), it executes the normal antenna switching process shown in FIG. 4 (step S104), and when the synchronization signal is not detected (No at step S103), it executes the synchronization restore antenna switching process for restoring the synchronization shown in FIG. 6 (step S105). After step S104 or S105, the selection controller C2 selects the antenna with maximum strength so as to connect and switch to it (step S106). Thereafter, the selection controller C2 repeats the process from step S102 until a predetermined process end instruction is given.

Figure 8:
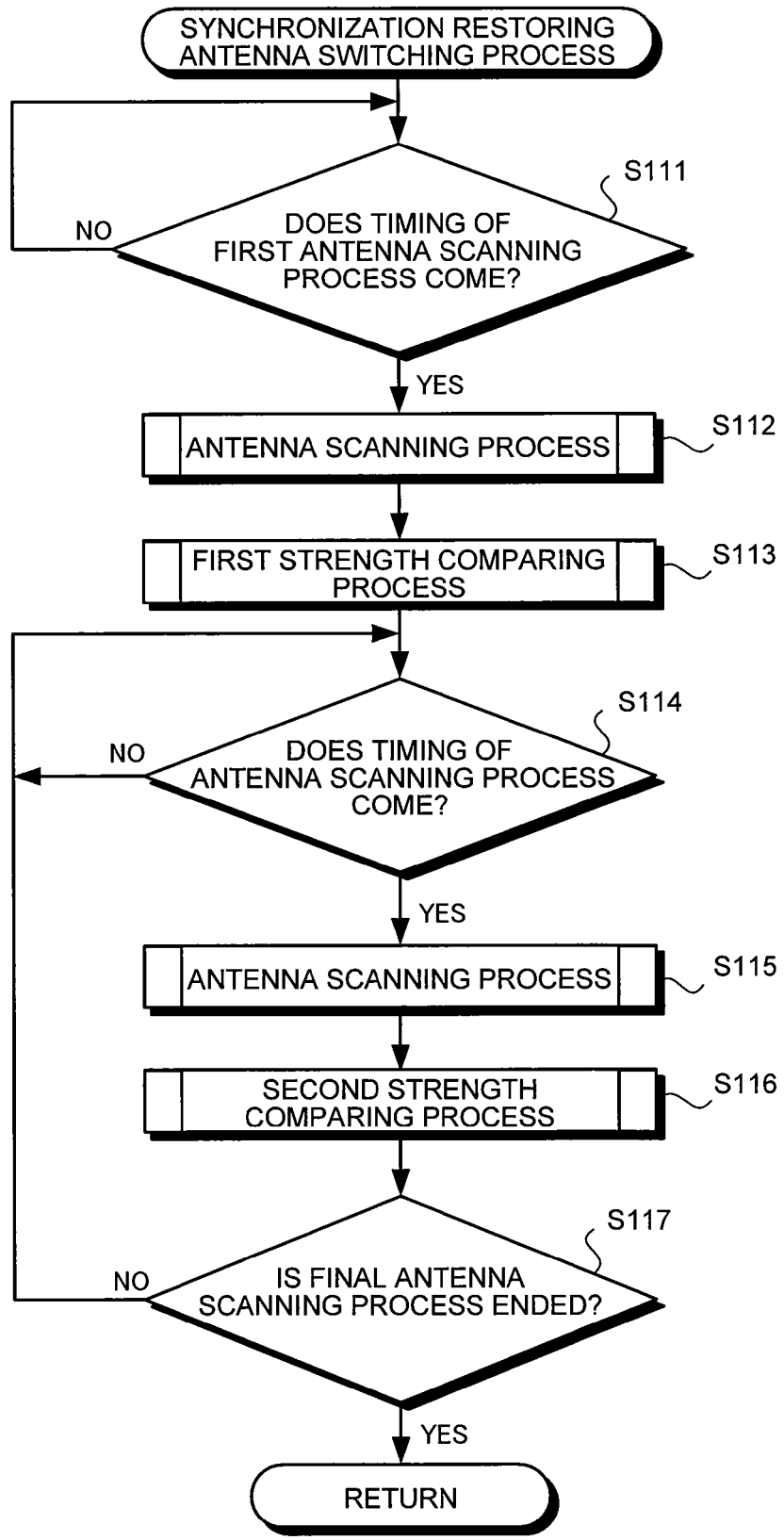
FIG. 8 is a flowchart illustrating the procedure of a synchronization restoring antenna switching process shown in FIG. 7.

The procedure of the synchronization restore antenna switching process will be explained below with reference to a flowchart shown in FIG. 8. As shown in FIG. 8, the selection controller C2 determines whether or not the timing of the first antenna scanning process in the scan repeating process comes on the basis of the internal clock (step S111), and when the timing of the antenna scanning process does not come (No at step S111), it repeats this determining process and stands by until predetermined timing comes.

When the timing of the antenna scanning process comes (Yes at step S111), the selection controller C2 switches the antennas 6a to 6h sequentially, for example, in order of the series of the antenna numbers, executes the antenna scanning process for recording the received strengths of the respective antennas (step S112), and executes a first strength comparing process for comparing the received strengths of the antennas as the result of the scanning process so as to record information about the antenna with maximum strength (step S113).

Sequentially, the selection controller C2 determines whether or not the timing of the antenna scanning process after second time in the scan repeating process comes, namely, the time when a predetermined scan repeating cycle ST passes from the starting time of the antenna scanning process comes (step S114). When the timing of the antenna scanning process does not come (No at step S114), the selection controller C2 repeats this determining process and stands by until the predetermined timing comes. When the timing of the antenna scanning process comes (Yes at step S114), the selection controller C2 executes the antenna scanning process (step S115), and executes a second strength comparing process for comparing the received strengths of the antennas as the result of the antenna scanning process so as to update and record the information about the antenna with largest strength (step S116).

Thereafter, the selection controller C2 determines whether or not the predetermined final antenna scanning process in the scan repeating process is completed (step S117). When the final antenna scanning process is not completed (No at step S117), the selection controller C2 repeats the process from the step s114, and when the final antenna scanning process is completed (Yes at step S117), the process returns to step S105.

Figure 9:
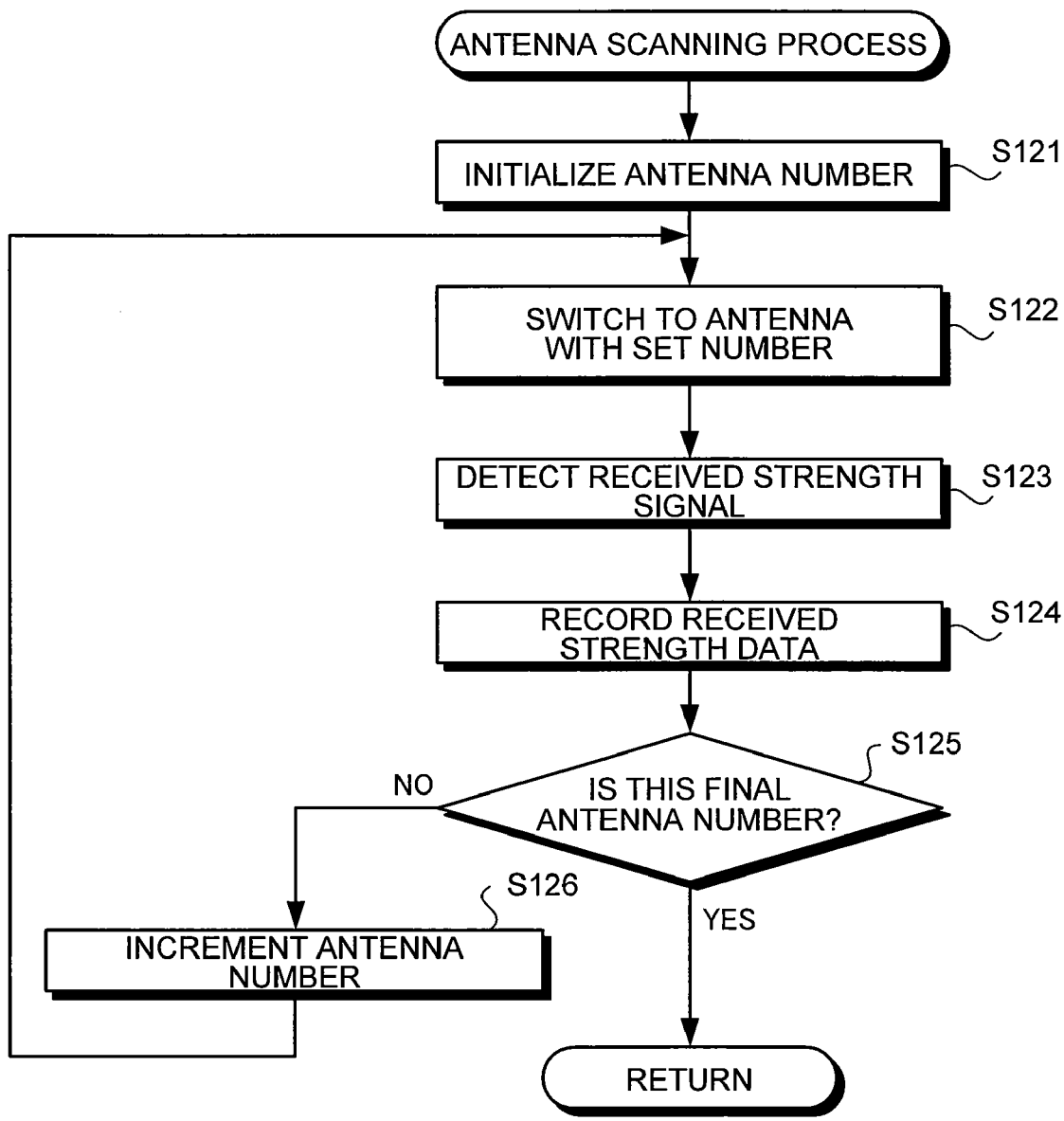
FIG. 9 is a flowchart illustrating the procedure of an antenna scanning process shown in FIG. 8.

The procedure of the antenna scanning process at steps S112 and S115 will be explained below with reference to a flowchart shown in FIG. 9. As shown in FIG. 9, the switching controller C2c provided to the selection controller C2 initializes the antenna number of the antenna for the first reception in the antenna scanning process (step S121). The switching controller C2c selects to set the antenna number 1, for example, at step S121.

The switching controller C2c switches the connection to the antenna with the antenna number set at steps S121 (step S122), detects a received strength signal via the A/D converter 16 (step S123), and records the detected received strength data into the strength storage unit C2a (step S124). At step S124, the switching controller C2c associates the received antenna numbers with the antennas so as to record the received strength data.

Thereafter, the switching controller C2c determines whether or not the connected antenna has the final antenna number in the antenna scanning process, for example, the antenna number 8 (step S125). When the connected antenna does not have the final number (No at step S125), it increments the antenna number (step S126) and executes the process from the step S122. When the connected antenna has the final number (Yes at step S125), the sequence returns to the original processing step, namely, step S112 or S115.

Figure 10:
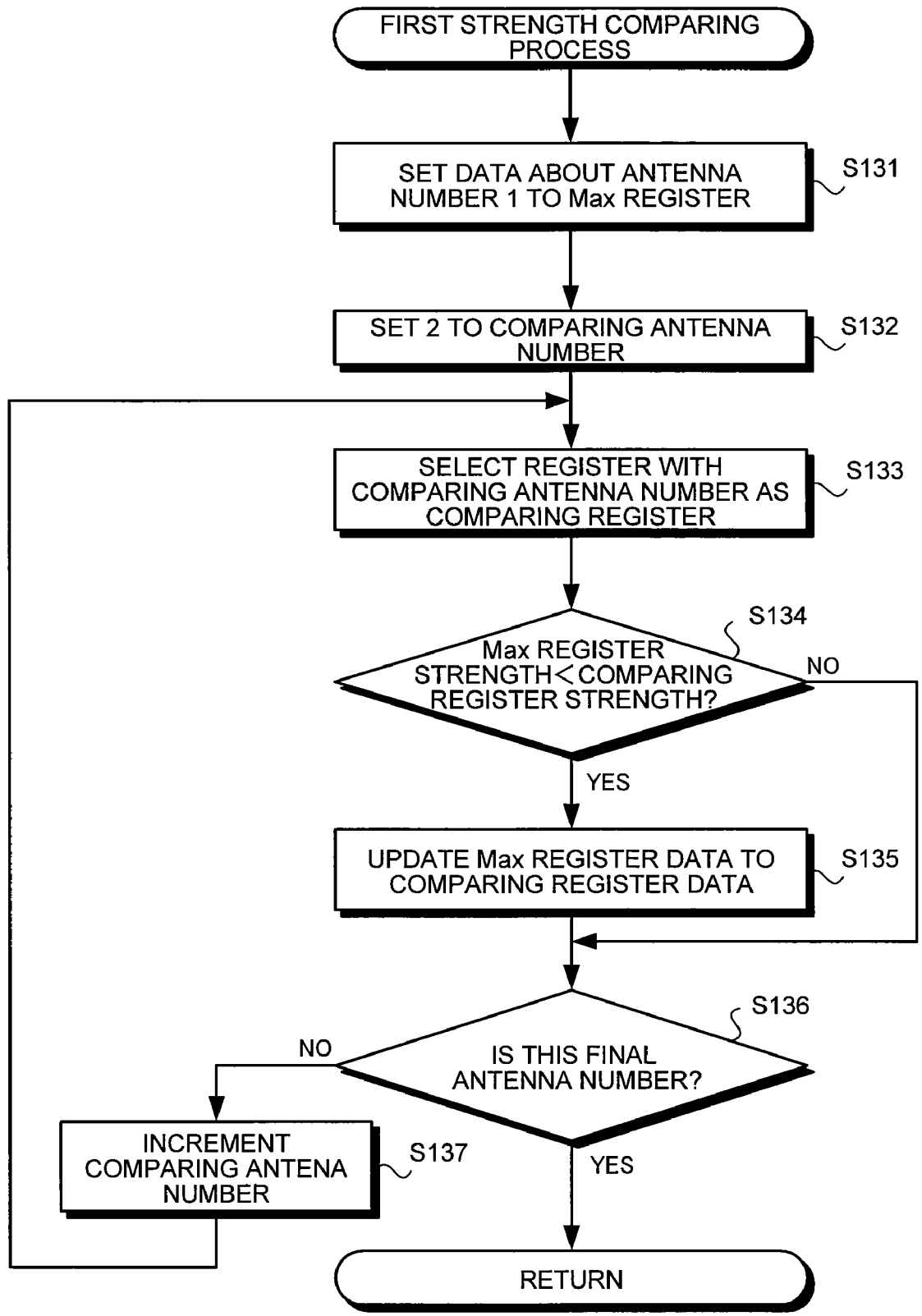
FIG. 10 is a flowchart illustrating the procedure of a first strength comparing process shown in FIG. 8.

Then, the procedure of the first strength comparing process at step S113 will be explained below with reference to a flowchart shown in FIG. 10. As shown in FIG. 10, the strength comparator C2b provided to the selection controller C2 refers to the received strength data recorded in the strength storage unit C2a and sets the received strength data of the antenna number 1 in the first antenna scanning process temporarily to a Max register corresponding to the maximum strength antenna in the strength storage unit C2a (step S131). Further, the antenna number 2 is set to a comparison antenna number showing the antenna whose received strength data are compared with those of the antenna with temporary maximum strength (step S132).

Subsequently, the strength comparator C2b selects the register corresponding to the comparison antenna number in the strength storage unit C2a as a comparison register (step S133), and determines whether or not the received strength recorded in the Max register (Max register strength) is smaller than the received strength recorded in the comparison register (comparison register strength) (step S134). When the Max register strength is smaller than the comparison register strength (Yes at step S134), the strength comparator C2b updates the data in the Max register to the data in the comparison register (step S135), and determines whether or not the comparison antenna number corresponding to the comparison register is the final number in the series of the antenna numbers, for example, the antenna number 8 (step S136). On the other hand, when the Max register strength is not smaller than the comparison register strength (No at step S134), the sequence goes directly to step S136.

When the strength comparator C2b determines that the comparison antenna number is not the final antenna number (No at step S136), it increments the comparison antenna number (step S137) so as to repeat the process from step S133. Further, when the strength comparator C2b determines that the comparison antenna number is the final antenna number (Yes at step S136), the sequence returns to step S113.

Figure 11:
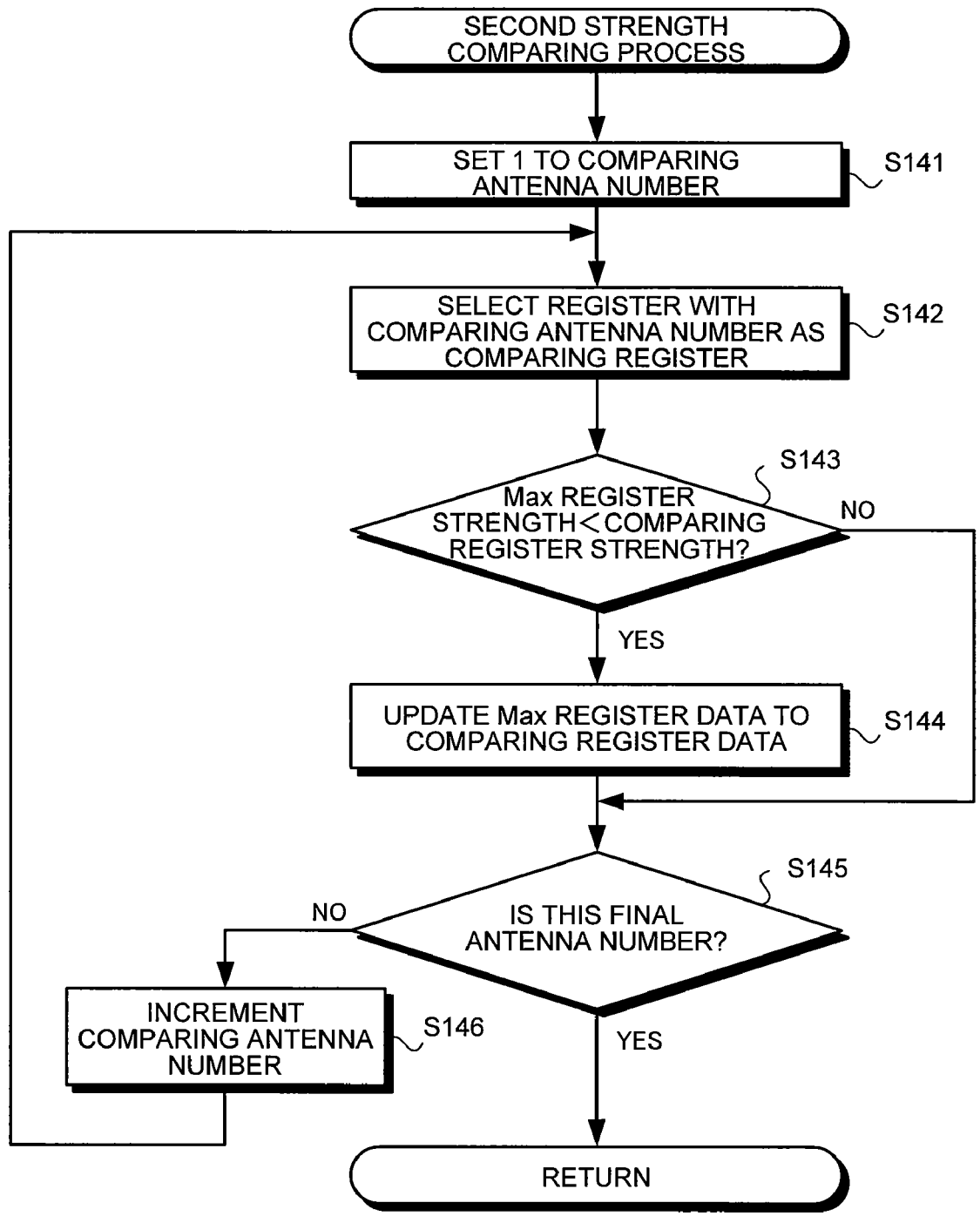
FIG. 11 is a flowchart illustrating the procedure of a second strength comparing process shown in FIG. 8.

The procedure of the second strength comparing process at step S116 will be explained below with reference to a flowchart shown in FIG. 11. At the second strength comparing process, as is clear from the comparison of the flowcharts in FIGS. 11 and 10, the antenna number 1 is firstly set as the comparison antenna number (step S141), and then, the same process as steps S133 to S137 in the first strength comparing process is executed at steps S142 to S146. The data in the Max register at the time of the completion of the first strength comparing process are diverted to the data in the Max data for first comparison in the second strength comparing process.

In the synchronization restore antenna switching process, the received strengths in the respective antennas in the antenna scanning processes are sequentially compared by the first and second strength comparing processes, the antenna number having the largest received strength is recorded in the Max register, and the antenna having the antenna number finally recorded in the Max register is detected as the antenna with maximum strength.

More concretely, in the case where the received strength data shown in FIG. 12, for example, are recorded, the received strengths of the antenna numbers 1 to 8 are sequentially compared in the first strength comparing strength corresponding to a first antenna scanning period AS1, and finally the received strength "80" of the antenna number 1 is recorded in the Max register. Further, in the second strength comparing process corresponding to a second antenna scanning period AS2, the received strengths of the antenna numbers 1 to 8 are sequentially compared on the basis of the Max register finally recorded at the antenna scanning period SA1. As a result, the data in the Max register as the basis, namely, the received strength "80" of the antenna number 1 is recorded as the final Max register.

Further, in the second strength comparing process corresponding to a final (third) antenna scanning period AS3, similarly to the second one, the received strengths of the antenna numbers 1 to 8 are sequentially compared on the basis of the Max register finally recorded at the antenna scanning period AS2. As a result, the data in the Max register as the basis, namely the received strength "80" of the antenna number 1 is recorded directly as the final Max register. The antenna 6a corresponding to the antenna number 1 recorded in the final Max register is detected as the antenna with maximum strength.

In the antenna scanning process and the first and second strength comparing processes, the antenna number is switched sequentially starting from No. 1. However, the switching is not necessarily limited to this, and for example, the antenna number may be sequentially switched randomly without overlapping.

Further, the normal antenna switching process at step S104 in the antenna switching process shown in FIG. 7 is realized by the process similar to the first antenna switching process in the synchronization restore antenna switching process shown in FIG. 8, namely, the antenna scanning process at step S112 and the first strength comparing process at step S113.

As explained above, in the case where the synchronization signal is not received by an antenna selected in advance in the receiving apparatus 2 according to the embodiment, the selection controller C2 repeats the antenna switching process for sequentially switching to the antennas 6a to 6h so as to measure the received strengths of the antennas in a shorter cycle than the signal-on period NT as the transmission period of the transmission information of the radio signal, so as to detect the antenna with maximum strength and select and switch to the detected antenna with maximum strengths the receiving antenna for receiving the synchronization information. For this reason, the selection controller C2 can restore the synchronization quickly and securely at the time when the synchronization signal is not received. Further, when the selection controller C2 repeats the antenna switching process for detecting the antenna with maximum strength for a period longer than the signal-off period FT as the non-transmission period obtained by subtracting the transmission period of the transmission information from the transmission period of the radio signal, the synchronization can be restored more quickly and securely. As a result, certainty and reliability of the receiving operating in the receiving apparatus 2 can be further improved.

Modification

A modification of the embodiment will be explained below. In the above embodiment, when the synchronization signal is not received, the selection controller C2 repeats the antenna scanning process intermittently at the predetermined scan repeating cycle ST. In this modification, however, it repeats the antenna scanning process continuously.

Figure 13:
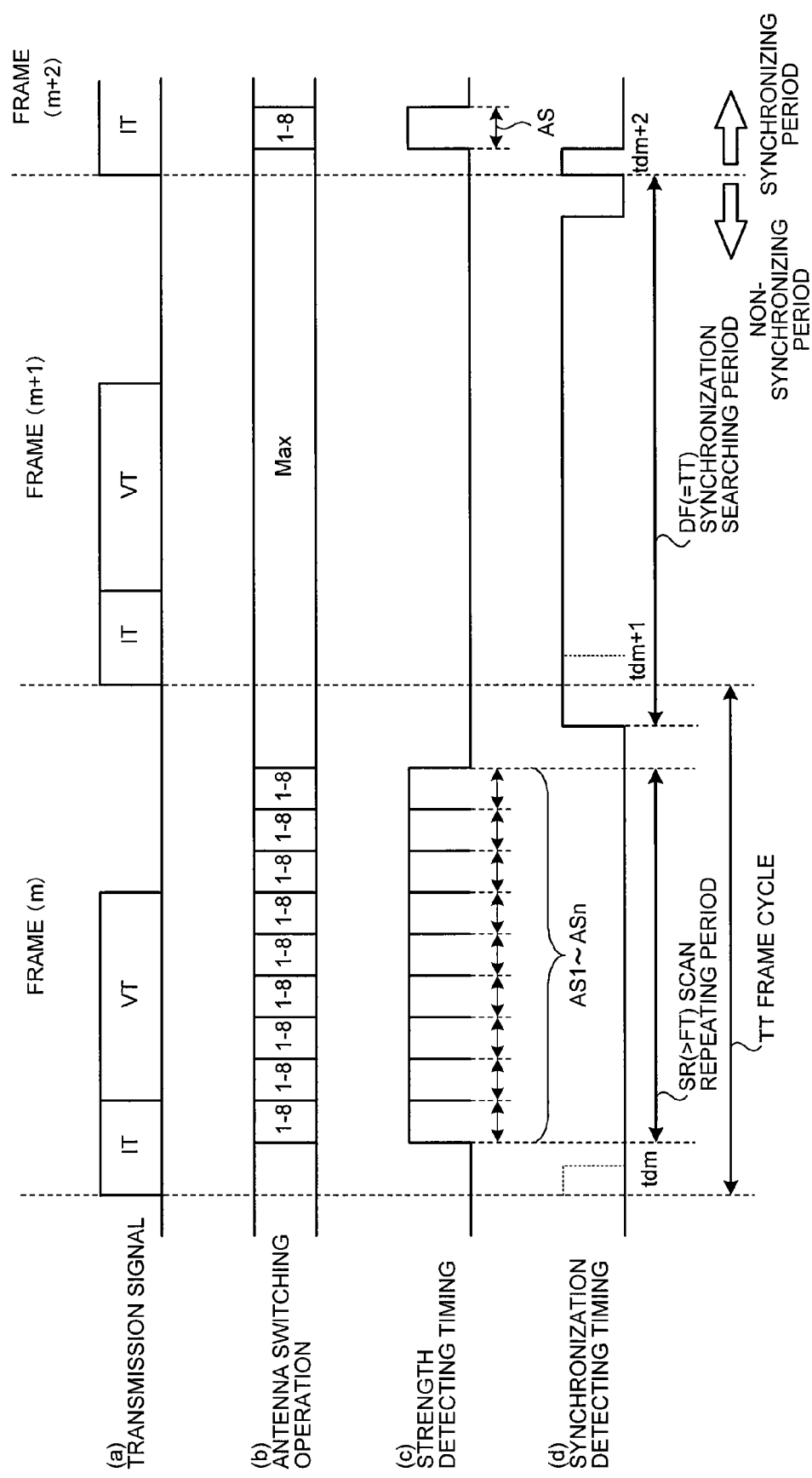
FIG. 13 is a time chart illustrating the antenna switching process as a modification in the case where a synchronization signal is not received.

FIG. 13 is a time chart illustrating the antenna switching process in the case where the synchronization signal is not received, the process being executed by the selection controller C2 in this modification. As shown in FIG. 13, when the synchronization signal is not received by the antenna selected in advance, for example, when the synchronization signal of the frame (m) is not received at timing $td_m$, the selection controller C2 controls the changeover switch SW, so that the scan repeating process for continuously repeating the antenna scanning process is executed.

Further, the selection controller C2 makes controls the scan repeating process so that this process is executed for the scan repeating period SR longer than the signal-off period FT. In the example shown in FIG. 13, the antenna scanning process is continuously repeated n times correspondingly to the antenna scanning periods AS1 to ASn within the scan repeating period SR. The scan repeating process in this modification, corresponds to the case where the scan repeating cycle ST of the scan repeating process in the above embodiment is approximately equal to the antenna scanning period AS.

According to the scan repeating process in this modification, the selection controller C2 can execute the antenna scanning process at least once for the signal-on period similarly to the scan repeating process in the above embodiment. According to the antenna scanning process executed for the signal-on period, the respective received strengths of the antennas 6a to 6h can be measured securely, the antenna in the transmission signal receivable position can be detected, and the antenna with maximum strength can be detected.

After the antenna with maximum strength is detected in the scan repeating process, similarly to the above embodiment, the selection controller C2 selects and switches to the detected antenna with maximum strength as the receiving antenna for receiving the synchronization signal so as to execute the synchronous searching process.

At the time when the antenna with maximum strength is detected, namely, at the time when the respective received strengths of the antenna 6a to 6h are securely measured, the selection controller C2 ends the scan repeating process and can start the synchronous searching process.

Figure 14:
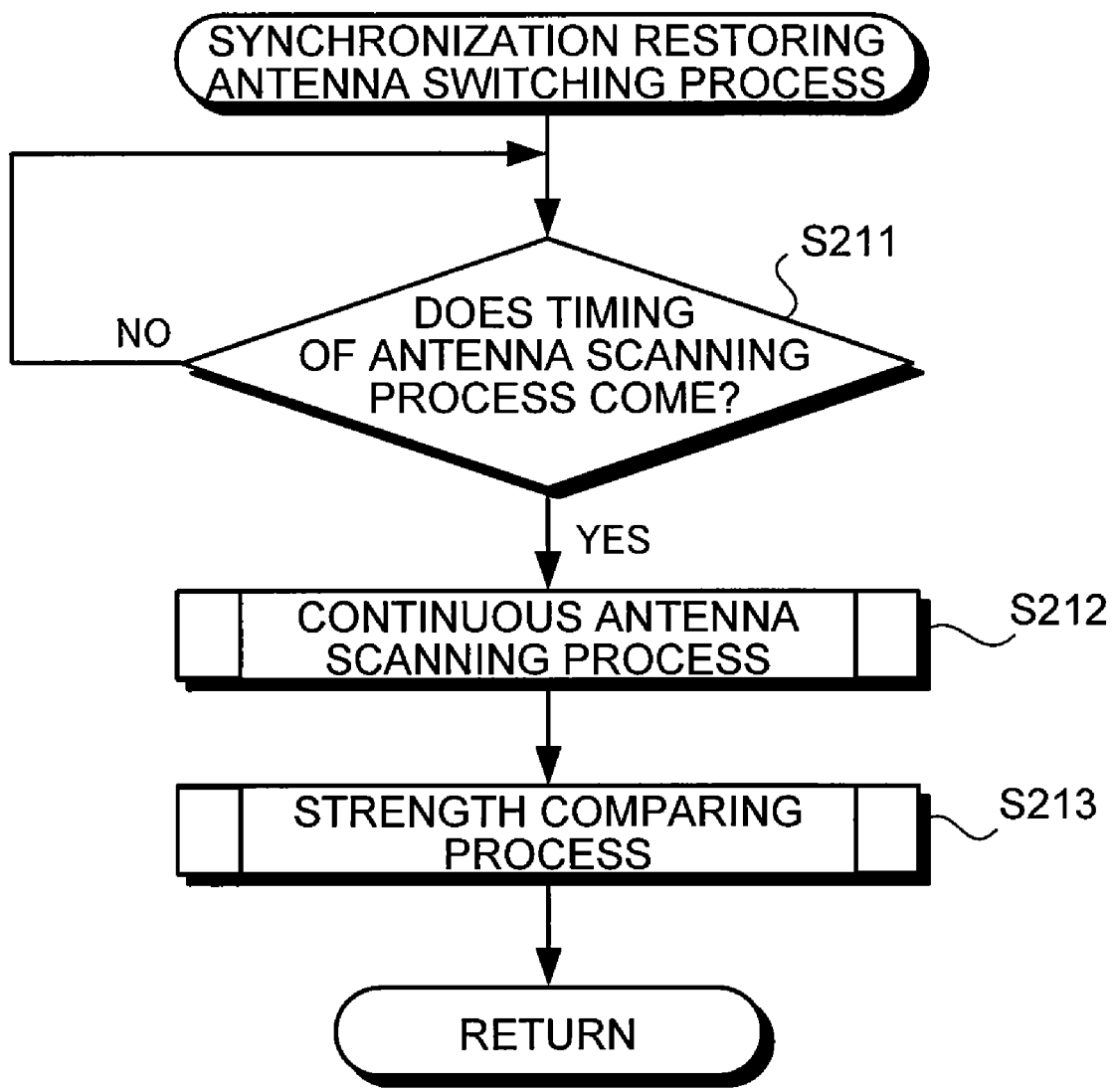
FIG. 14 is a flowchart illustrating the procedure of the synchronization restoring antenna switching process as a modification.

The procedure of the synchronous restore antenna switching process in this modification will be explained below with reference to a flowchart shown in FIG. 14. The synchronous restore antenna switching process is a process to be executed as step S105 shown in FIG. 7. As shown in FIG. 14, the selection controller C2 firstly determines whether or not the timing of the first antenna scanning process in the scan repeating process comes on the bases of the internal clock (step S211), and when the timing of the antenna scanning process does not come (No at step S211), it repeats this determining process so as to stand by until predetermined timing comes.

When the timing of the antenna scanning process comes (Yes at step S211), the selection controller C2 executes the continuous antenna scanning process to be continuously executed (step S212), and executes the strength comparing process for comparing the received strengths of the respective antennas in the respective antenna scanning process as the result of the continues antenna scanning process so as to detect the antenna with maximum strength (step S213), and the sequence returns to step S105.

Figure 15:
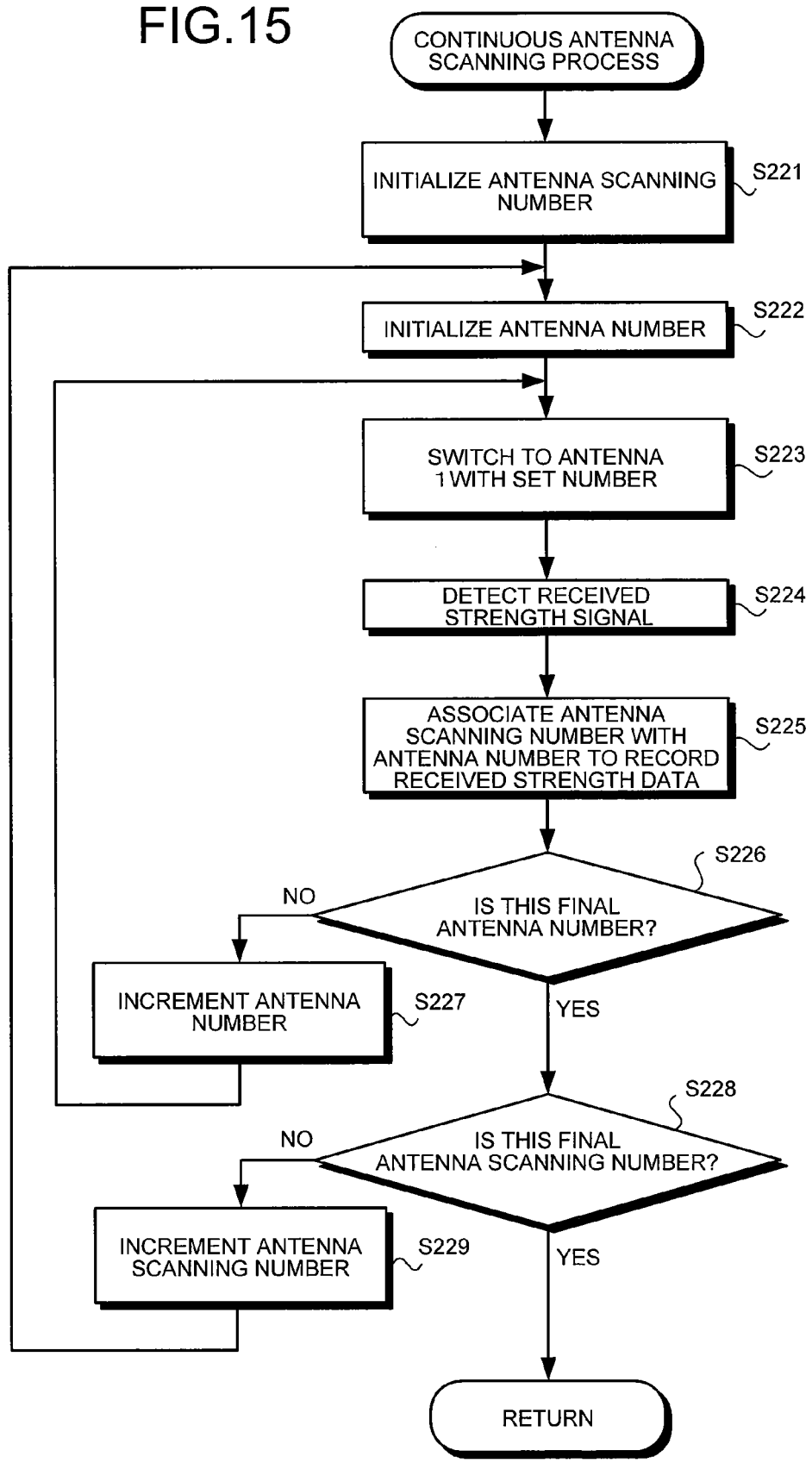
FIG. 15 is a flowchart illustrating the procedure of a continuous antenna scanning process shown in FIG. 14.

The procedure of the continuous antenna scanning process at step S212 will be explained below with reference to a flowchart shown in FIG. 15. As shown in FIG. 15, the switching controller C2c initializes the antenna scanning number representing the processing times of the antenna scanning processes repeated in the continuous antenna scanning process (step S221). At step S221, for example, "1" is set as the initial value. Further, the switching controller C2c initializes the antenna number of the antenna for first reception (step S222). The switching controller C2c selects and sets the antenna number 1, for example, at step S222.

Subsequently, the switching controller C2c switches the connection to the antenna with antenna number set at step S222 (step S223), detects a received strength signal via the A/D converter 16 (step S224), and associates the antenna scanning number with the antenna number so as to record the received strength data into the strength storage unit C2a (step S225).

Thereafter, the switching controller C2c determines whether or not the connected antenna has the final antenna number in the current antenna scanning process, for example, the antenna number 8 (step S226), and when this antenna does not have the final number (No at step S226), it increments the antenna number (step S227) so as to repeat the process from step S223.

On the other hand, when the antenna number has the final number (Yes at step S226), the switching controller C2c determines whether or not the current antenna scanning number is the final antenna scanning number in the continuous antenna scanning process (step S228). When the current antenna number is not the final number (No at step S228), the switching controller C2c increments the antenna scanning number (step S229) so as to repeat the process from step S222. When the antenna scanning number is the final number (Yes at step S228), the sequence returns to step S212.

The strength comparing process at step S213 shown in FIG. 14 will be explained below. The strength comparing process is executed similarly to the first strength comparing process shown in FIG. 10. In the strength comparing process, the antenna number which is sequentially switched as the comparison antenna number is the respective antenna numbers in the series of the antenna scanning processes for switching and connection in the continuous antenna scanning process. In this case, for example, the antenna number is sequentially switched from the antenna number 1 of the antenna scanning number "1" through the antenna number 8 of the antenna scanning number "n" in antenna numerical order and the antenna scan numerical order, so that the received strength data are compared and the antenna with maximum strength is detected. Data about the antenna number 1 in the antenna scanning number "1", for example, may be used as the data to be set as the initial setting in the Max register.

In the above embodiments, as shown in FIG. 4, as the normal antenna switching process in the case where the synchronization signal is received, the antenna scanning process is executed within the received strength measuring period and the antenna with maximum strength is detected, so that the detected antenna with maximum strength is used as the receiving antenna for the image signal period, but this process is not necessarily limited to the antenna switching process, and thus for example, the process may be executed as shown in a time chart shown in FIG. 16, for example.

That is, in the antenna switching process shown in FIG. 16, the selection controller C2 measures the received strength of the antenna with antenna number 2, for example, at the timing $t1_n$ within the received strength measuring period (IT) of the frame (n). Further, the selection controller C2 measures the received strength of the antenna with antenna number 1, for example, at the timing $t2_n$ within the image signal period (VT) of the same frame (n). The selection controller C2 compares these measured received strengths, and when the received strength measured for the received strength measuring period exceeds the received strength measured for the image signal period, it selects and switches to the antenna (for example, No. 2) measured for the received strength measuring period as the receiving antenna for the image signal period of the next frame (n+1). Further, the selection controller C2 selects and switches to the antenna (for example, No. 2) measured for the reception measuring period as the receiving antenna of the image signal period of the next frame (n+1). The selection controller C2 also controls the antenna switching process so that this process is repeated while the antenna corresponding to the received strength measuring period is being sequentially switched at each frame.

Specifically, in FIG. 16, the received strength of the antenna number 2 does not exceed the received strength of the antenna number 1 at the frame (n). For this reason, the receiving antenna at the image signal period is the antenna of No. 1 at the frame (n+1). On the other hand, the receiving antenna at the received strength measuring period at the frame (n+1) is switched into the antenna of No. 3. Since the received strength of the antenna number 3 exceeds the received strength of the antenna number 1 at the frame (n+1), the antenna number 3 is selected as the receiving antenna at the image signal period at the frame (n+1). At the same time, the receiving antenna at the received signal measuring period at the frame (n+2) is switched into the antenna of No. 4.

In the embodiment and the modification, the receiving apparatus of the present invention is applied to a wireless in-vivo information acquiring system, and receives a radio signal transmitted from the capsule endoscope. The present invention is, however, not limited to this, and the radio signal to be received may be an arbitrary radio signal as long as it has transmission information including at least the synchronization information transmitted in the predetermined transmission cycle, and a transmission apparatus for transmitting such a radio signal is not limited.

INDUSTRIAL APPLICABILITY

As mentioned above, the receiving apparatus of the present invention is effective for selectively receiving a radio signal having transmission information including at least synchronization information transmitted in a predetermined transmission cycle by using a plurality of antennas, and is particularly suitable for receiving a radio image signal transmitted from a capsule endoscope in a subject by using a plurality of antennas outside the subject.

The invention claimed is:

1. A receiving apparatus which selectively receives a radio signal through a plurality of antennas, the radio signal having transmission information including at least synchronization information transmitted in a predetermined transmission cycle, the receiving apparatus comprising:
a control unit which is configured to:
select one of the antennas to obtain a selected antenna;
determine whether the synchronization information is detected in the transmission information received through the selected antenna;
repeat an antenna switching process in a cycle shorter than a transmission period of the transmission information, if the synchronization information is not detected in the transmission information through the selected antenna, the antenna switching process continuously switching between the antennas to measure received electric field strengths of the respective antennas; and
make a control for detecting an antenna with maximum strength whose received electric field strength is the largest, and selecting and switching to the antenna with maximum strength as a receiving antenna for receiving the synchronization information.

2. The receiving apparatus claim 1, wherein the control unit gives a series of antenna numbers to the plurality of antennas, respectively and switches between the antennas in an antenna numerical order to execute the antenna switching process.

3. The receiving apparatus claim 1, wherein after the control unit selects and switches to the antenna with maximum strength as the receiving antenna for receiving the synchronization information, the control unit makes a control for continuing a connection until at least the synchronization information is received.

4. The receiving apparatus claim 1, wherein
the transmission information includes an information main body section including an information main body and an adding section including the synchronization information, and
when the synchronization information is detected through the selected antenna, the control unit sequentially switches between the plurality of antennas for a transmission period of the adding section to measure received electric field strengths of the antennas, and selects and switches to an antenna having the largest received electric field strength as a receiving antenna for receiving the information main body section.

5. The receiving apparatus according to claim 1, wherein
the radio signal is a signal having a frame constitution having an information main body section including an information main body and an adding section including the synchronization information, and
when the synchronization information of a current frame is detected through the selected antenna, the control unit measures a received electric field strength of a first antenna within a transmission period of the adding section of the current frame, measures a received electric field strength of a second antenna within a transmission period of the information main body section of the current frame, and when the received electric field strength of the first antenna exceeds the received electric field strength of the second antenna, the control unit selects and switches to the first antenna as a receiving antenna for receiving the information main body section of a next frame.

6. The receiving apparatus according claim 1, wherein
the radio signal is a signal which is transmitted from a transmission apparatus, the transmission apparatus being introduced into a subject and moving in the subject, and
the information main body includes in-vivo image information obtained by imaging an inside of the subject.

7. A receiving apparatus which selectively receives a radio signal through a plurality of antennas, the radio signal having transmission information including at least synchronization information transmitted in a predetermined transmission cycle, the receiving apparatus comprising:
a control unit which is configured to:
select one of the antennas to obtain a selected antenna;
determine whether the synchronization information is detected in the transmission information received through the selected antenna;
repeat an antenna switching process for a period longer than a non-transmission period obtained by subtracting a transmission period from the transmission cycle, if the synchronization information is not detected in the transmission information through the selected antenna, the antenna switching process continuously switching between the antennas to measure received electric field strengths of the respective antenna; and
make a control for detecting an antenna with maximum strength whose received electric field strength is the largest, and selecting and switching to the antenna with maximum strength as a receiving antenna for receiving the synchronization information.

8. The receiving apparatus according to claim 7, wherein the control unit makes a control for continuously repeating the antenna switching process.

9. The receiving apparatus according to claim 7, wherein the control unit gives a series of antenna numbers to the plurality of antennas, respectively and switches between the antennas in an antenna numerical order to execute the antenna switching process.

10. The receiving apparatus according to claim 7, wherein after the control unit selects and switches to the antenna with maximum strength as the receiving antenna for receiving the synchronization information, the control unit makes a control for continuing a connection until at least the synchronization information is received.

11. The receiving apparatus according to claim 7, wherein
the transmission information includes an information main body section including an information main body and an adding section including the synchronization information, and when the synchronization information is detected through the selected antenna, the control unit sequentially switches between the plurality of antennas for a transmission period of the adding section to measure received electric field strengths of the antennas, and selects and switches to an antenna having the largest received electric field strength as a receiving antenna for receiving the information main body section.

12. The receiving apparatus according to claim 7, wherein the radio signal is a signal having a frame constitution having an information main body section including an information main body and an adding section including the synchronization information, and when the synchronization information of a current frame is detected through the selected antenna, the control unit measures a received electric field strength of a first antenna within a transmission period of the adding section of the current frame, measures a received electric field strength of a second antenna within a transmission period of the information main body section of the current frame, and when the received electric field strength of the first antenna exceeds the received electric field strength of the second antenna, the control unit selects and switches to the first antenna as a receiving antenna for receiving the information main body section of a next frame.

13. The receiving apparatus according to claim 7, wherein the radio signal is a signal which is transmitted from a transmission apparatus, the transmission apparatus being introduced into a subject and moving in the subject, and the information main body includes in-vivo image information obtained by imaging an inside of the subject.

14. A receiving apparatus which selectively receives a radio signal through a plurality of antennas, the radio signal having transmission information including at least synchronization information transmitted in a predetermined transmission cycle, the receiving apparatus comprising:

a control unit which is configured to:

select one of the antennas to obtain a selected antenna;

determine whether the synchronization information is detected in the transmission information received through the selected antenna;

perform an antenna switching process, if the synchronization information is not detected in the transmission information through the selected antenna, the antenna switching process continuously switching between the plurality of antennas to measure received electric field strengths of the respective antennas; and record the received electric field strengths of the respective antennas in association with an antenna scanning number and an antenna number of the antenna selected, the antenna scanning number representing the processing times of the antenna switching processes repeated.

* * * * *